US012691097B2

(12) United States Patent
Atwood et al.

(10) Patent No.: US 12,691,097 B2
(45) Date of Patent: Jul. 28, 2026

(54) METHODS AND COMPOSITIONS FOR TREATING POLYOMAVIRUS

(71) Applicant: Brown University, Providence, RI (US)

(72) Inventors: Walter J. Atwood, Rumford, RI (US); Jacob S. Kaiserman, Garden City, NY (US)

(73) Assignee: BROWN UNIVERSITY, Providence, RI (US)

( * ) Notice: Subject to any disclaimer, the term of this patent is extended or adjusted under 35 U.S.C. 154(b) by 417 days.

(21) Appl. No.: 18/224,304

(22) Filed: Jul. 20, 2023

(65) Prior Publication Data

US 2024/0024283 A1 Jan. 25, 2024

Related U.S. Application Data

(60) Provisional application No. 63/391,128, filed on Jul. 21, 2022.

(51) Int. Cl.
*A61K 31/404* (2006.01)
*A61P 31/20* (2006.01)

(52) U.S. Cl.
CPC ............ *A61K 31/404* (2013.01); *A61P 31/20* (2018.01)

(58) Field of Classification Search
CPC .............................. A61K 31/404; A61P 31/20
See application file for complete search history.

(56) References Cited

U.S. PATENT DOCUMENTS 10,864,210 B2 * 12/2020 Zou ...................... A61K 31/422

OTHER PUBLICATIONS

Martin et al. (Biochemical Society Transactions (2021), 49(1), 281-295).*

Zarrinhaghighi et al. (Trends in Pharmaceutical Sciences (2020), 6(1), 11-20).*

Kaiserman, Jacob, et al. "An elusive target: inhibitors of JC polyomavirus infection and their development as therapeutics for the treatment of progressive multifocal leukoencephalopathy." International Journal of Molecular Sciences 24.10 (2023): 8580.

Kaiserman, Jacob, et al. "The oxindole GW-5074 inhibits JC polyomavirus infection and spread by antagonizing the MAPK-ERK signaling pathway." Mbio 14.2 (2023): e03583-22.

* cited by examiner

*Primary Examiner* — Bruck Kifle
(74) *Attorney, Agent, or Firm* — K&L Gates LLP

(57) ABSTRACT

Described are compositions and methods for treating polyoma viruses such as JCPyV.

12 Claims, 6 Drawing Sheets

GW-5074
Inhibits Viral
Spread

* A: Multicycle growth assay
  * allowed for one round of productive infection (72 hours) before treating with 20μM GW-5074 or DMSO control
* B, C: harvested supernatant

GW-5074 Reduces Initial Infection by Human and Simian Polyomaviruses

SV40 does not require MAPK-ERK signaling to infect target cells.[1]

U0126: inhibits MAPK-ERK (MEK1/2)

| B | Cell Line | Virus(es) |
|---|-----------|-----------|
| | SVG-A | JCPyV, SV40 |
| | Vero | BKPyV |

GW-5074 Reduces Initial Infection by JCPyV in 1° Astrocytes

Transformation with SV40 T Antigen is known to affect virus-induced signaling events, including signals carried by the MAPK-ERK pathway (Wilcezk *et al.*, 2021).

| Cell Line | Type |
|---|---|
| SVG-A | Transformed with SV40 T-Antigen |
| NHA | Primary |

METHODS AND COMPOSITIONS FOR TREATING POLYOMAVIRUS

CROSS-REFERENCE TO RELATED APPLICATION

This application claims the benefit of, and priority to, U.S. Provisional Patent Application 63/391,128 filed Jul. 21, 2022, the entire contents of which is incorporated by reference herein.

GOVERNMENT LICENSE RIGHTS

This invention was made with government support under grant number R35 NS116836 awarded by the National Institutes of Health. The government has certain rights in the invention.

TECHNICAL FIELD

The present disclosure generally relates to the field of treatments for polyomavirus.

BACKGROUND

Polyomaviridae is a family of viruses whose natural hosts are primarily mammals and birds. As of 2020, there are six recognized genera and 117 species, five of which are unassigned to a genus. JC polyomavirus (JCPyV) is a DNA tumor virus with a double-stranded DNA genome and encodes a well-studied oncogene, large T antigen. Its host range is highly restricted to humans and only a few cell types support lytic infection in vivo or in vitro.

JCPyV is the causative agent of a fatal central nervous system disease known as progressive multifocal leukoencephalopathy (PML), a neurological disorder characterized by destruction of cells that produce myelin (the material that insulates nerve cells).

Polyomavirus infection itself is ubiquitous; between 60-80% of adults are seropositive for JCPyV. JCPyV is thought to persist in the kidneys, and asymptomatic individuals secrete virus in the urine. However, PML typically occurs in patients with lymphoproliferative and myeloproliferative diseases, solid organ malignancies, HIV (human immunodeficiency virus) infection, autoimmune diseases, and in patients on antirejection immunosuppressive drugs after organ transplantation or patients treated with immunomodulatory therapies such as natalizumab.

The first signs of PML can vary from person to person, depending on the nerves that are initially damaged, but the often include:

1. Clumsiness or loss of coordination;
2. Difficulty walking;
3. Facial drooping;
4. Loss of vision;
5. Personality changes;
6. Difficulty speaking;
7. Weak muscles; and
8. Seizures.

Initial cases of PML were mostly restricted to patients with lymphoproliferative disorders. Indeed. PML remained an obscure disease until the mid-1980s; just 230 cases of PML were recorded in the United States between 1958 and 1984. New York City physicians identified the first case of HIV-associated PML in 1982, and during the 1980s, epidemiological studies suggest that the incidence of PML increased nearly 50-fold compared to previous decades due to the spread of HIV/AIDS.

PML became an AIDS-defining illness, and HIV-associated PML is estimated to have occurred in up to 10% of HIV/AIDS cases. By the mid-2000s, the adoption of highly active antiretroviral therapy (HAART) significantly decreased the incidence and fatality of HIV-associated PML in the United States, Though HIV-associated PML is no longer the primary cause of PML, HIV-associated PML still accounts for –80% of PML cases and causes significant morbidity. Although PML has been known to scientists and physicians for nearly 70 years, there are no treatments for this disease. Accordingly, there is a need for effective methods of treating the disease, its underlying causes, and its symptoms.

SUMMARY

The present disclosure, in part, relates to compositions and methods for treating diseases and disorders such as, for example, PML. For example, disclosed herein are novel uses of Raf-1 inhibitors such as GW-5074 (3-(3,5-dibromo-4-hydroxybenzylidene)-5-iodoindolin-2-one):

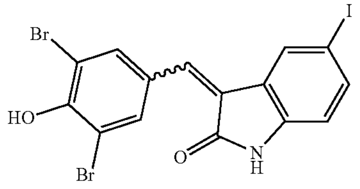 [SMILES: O=C1Nc2ccc(I)cc2C1=Cc1cc(Br)c(O)c(Br)c1]

Derivatives and analogs of GW-5074 are also within the scope of the present disclosure.

Disclosed embodiments comprise compositions. For example, disclosed compositions comprise GW-5074 and analogs and derivatives thereof. Disclosed compositions can further comprise a pharmaceutically acceptable carrier.

Also disclosed are kits comprising disclosed compositions, as well as instructions for use in disclosed methods.

DETAILED DESCRIPTION

Definitions

Figure 1:
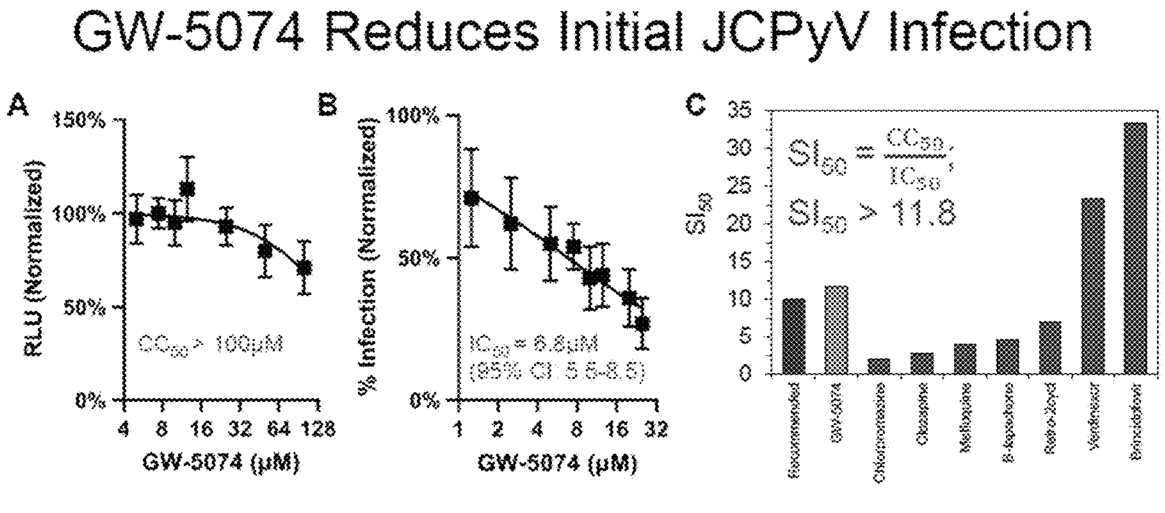
FIG. 1 illustrates the reduction in initial JCPyV infection demonstrated by GW-5074.
Figure 2:
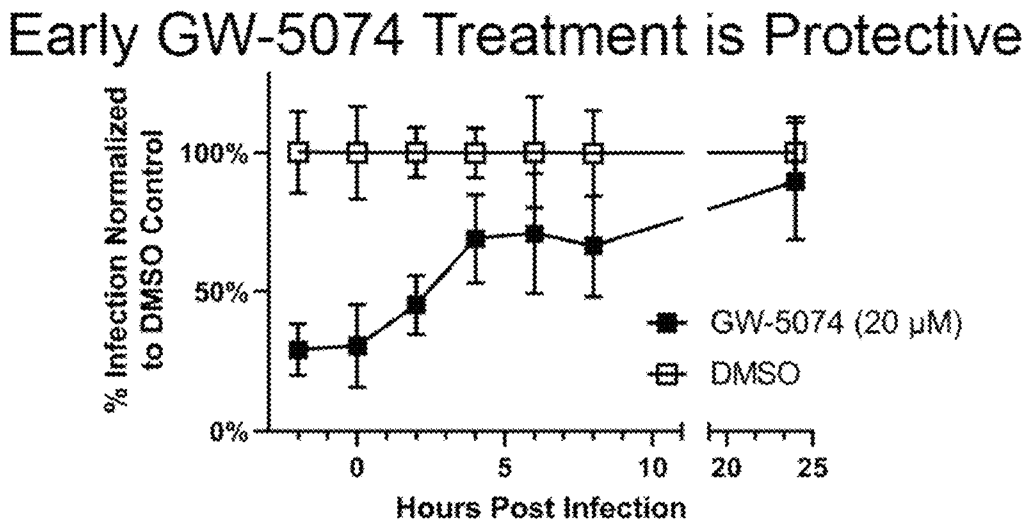
FIG. 2 illustrates the protective effect of GW-5074.
Figure 3:
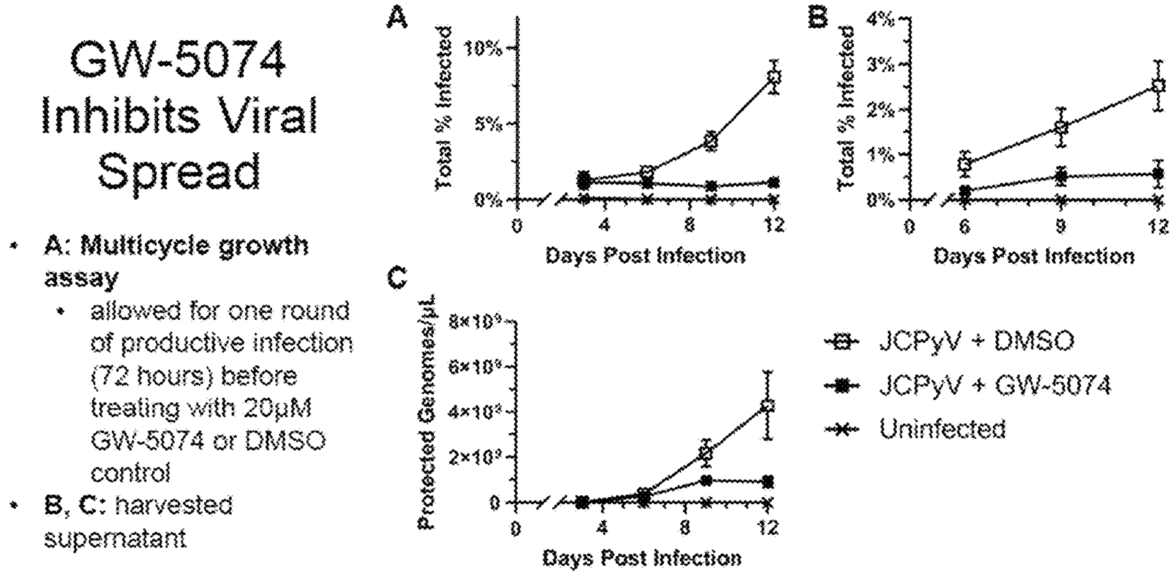
FIG. 3 shows inhibition of viral spread by GW-5074.
Figure 4:
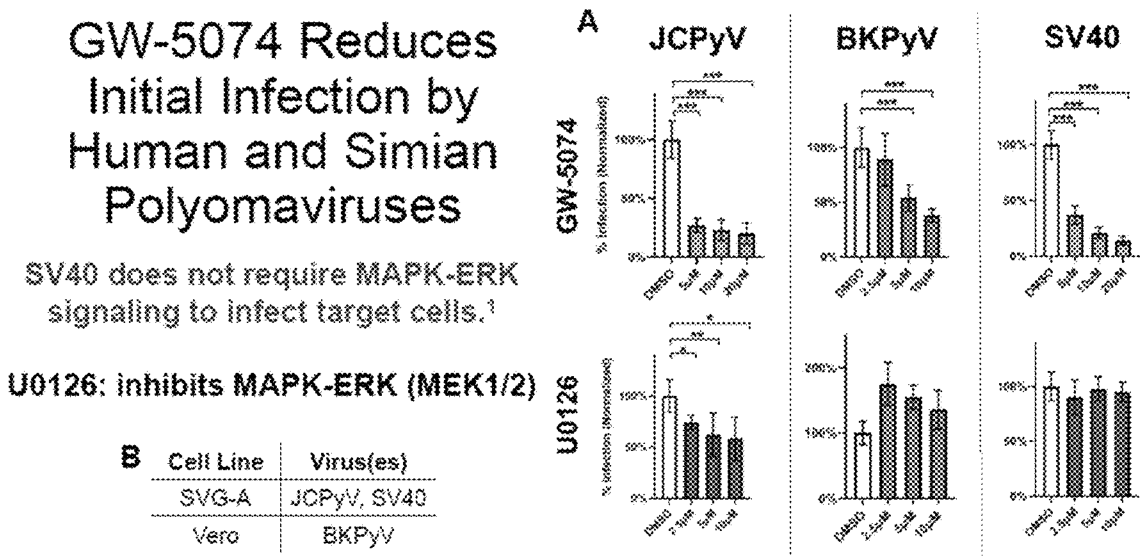
FIG. 4 shows reduction of initial infection demonstrated by GW-5074 against human and simian polyomaviruses.
Figure 5:
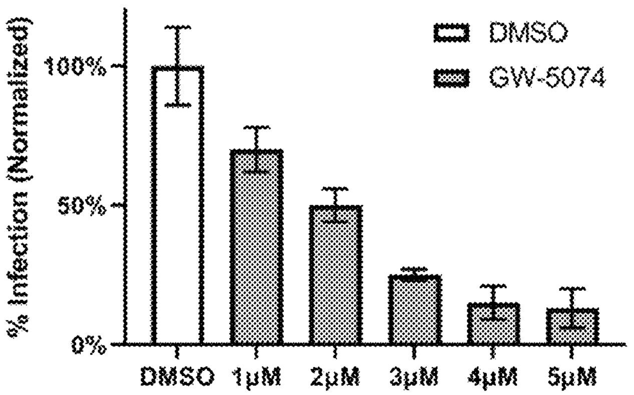
FIG. 5 shows reduction of initial infection demonstrated by GW-5074 against JCPyV in primary human astrocytes.
Figure 6:
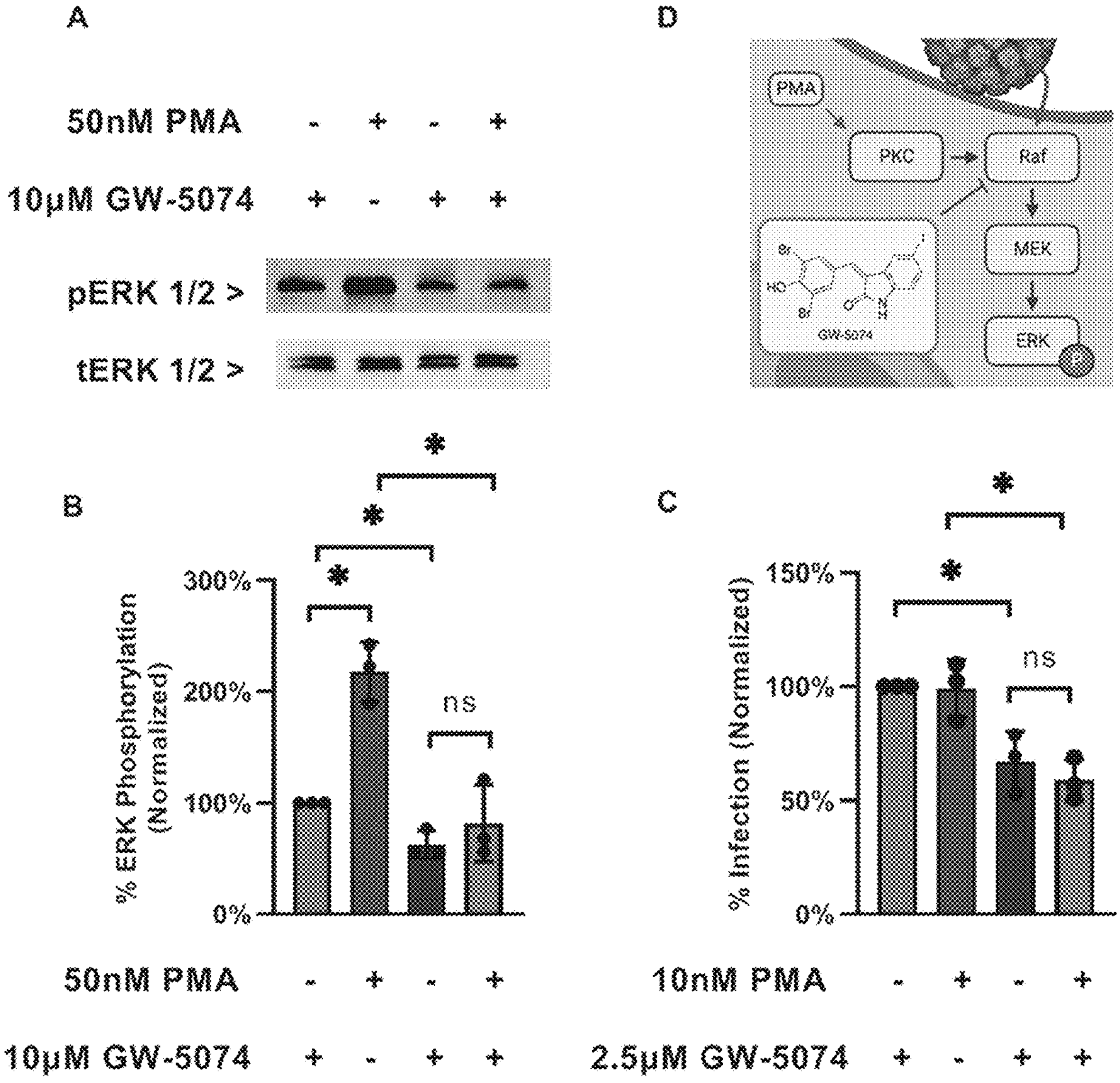
FIG. 6 shows that GW-5074 inhibits endogenous ERK1/2 phosphorylation.

Some definitions are provided hereafter. Nevertheless, definitions may be located in further sections below, and the above header "Definitions" does not mean that such disclosures in further sections below are not definitions.

"A" and "an" are used herein to refer to one or to more than one (i.e., to at least one) of the grammatical object of the article. By way of example, "an element" means one element or more than one element.

"Administration," or "to administer" means the step of giving (i.e. administering) a pharmaceutical composition or active ingredient to a subject. The pharmaceutical compositions disclosed herein can be administered via a number of appropriate routes including by injection.

"Comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

"Or" as used herein should be understood to mean "and/or", unless the context clearly indicates otherwise.

"Parenteral administration" and "administered parenterally" are art-recognized terms, and include modes of administration other than enteral and topical administration, such as injections, and include, without limitation, retro-orbital, intraocular, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

"Patient" means a human or non-human subject receiving medical or veterinary care.

"Pharmaceutically acceptable" or "therapeutically acceptable" refers to a substance which does not interfere with the effectiveness or the biological activity of the active ingredients and which is not toxic to a patient.

"Pharmaceutically acceptable carrier" is art-recognized, and includes, for example, pharmaceutically acceptable materials, compositions or vehicles, such as a liquid or solid filler, diluent, excipient, solvent, or encapsulating material, involved in carrying or transporting any subject composition from one organ, or portion of the body, to another organ, or portion of the body.

Each carrier must be "acceptable" in the sense of being compatible with the other ingredients of a subject composition and not injurious to the patient. In certain embodiments, a pharmaceutically acceptable carrier is non-pyrogenic.

Exemplary materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, sunflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

"Pharmaceutical composition" means a formulation comprising an active agent. The word "formulation" means that there is at least one additional ingredient (such as, for example and not limited to, an albumin [such as a human serum albumin or a recombinant human albumin] and/or sodium chloride) in the pharmaceutical composition in addition to an active agent. A pharmaceutical composition is therefore a formulation which is suitable for diagnostic, therapeutic or cosmetic administration to a subject, such as a human patient.

The pharmaceutical composition can be: in a lyophilized or vacuum dried condition, a solution formed after reconstitution of the lyophilized or vacuum dried pharmaceutical composition with saline or water, for example, or; as a solution that does not require reconstitution. As stated, a pharmaceutical composition can be liquid, semi-solid, or solid. A pharmaceutical composition can be animal-protein free.

"Reducing", "suppressing" and "inhibiting" have their commonly understood meaning of lessening or decreasing.

"Therapeutic formulation" means a formulation that can be used to treat and thereby alleviate a disorder or a disease and/or symptom associated thereof.

"Therapeutically effective amount" means the level, amount or concentration of an agent needed to treat a disease, disorder or condition without causing significant negative or adverse side effects.

"Treat," "treating," or "treatment" means an alleviation or a reduction (which includes some reduction, a significant reduction a near total reduction, and a total reduction), resolution or prevention (temporarily or permanently) of a symptom, disease, disorder or condition, so as to achieve a desired therapeutic or cosmetic result, such as by healing of injured or damaged tissue, or by altering, changing, enhancing, improving, ameliorating and/or beautifying an existing or perceived symptom, disease, disorder or condition.

Polyomaviruses such as JCPyV and BK polyomavirus (BKPyV) cause significant morbidity and mortality in immunosuppressed or immunomodulated patients. Diseases caused by these viruses are rare, however the group at risk is large.

A synthetic oxindole, GW-5074, was originally developed to inhibit C-Raf Kinase (MAPK-ERK), and has been well-tolerated in Phase I human trials when co-administered with sorafenib by IV to treat solid tumors. The 50% selectivity index ($SI_{50}$) of this drug is significantly higher than other drugs or compounds that have known activity against polyomaviruses. $SI_{50}$s>10 are commonly used to identify promising clinical candidates.

Disclosed compositions and methods provide novel, effective compositions and methods for treating polyomaviruses.

Compositions

Disclosed embodiments comprise compositions, for example compositions comprising a synthetic oxindole such as GW-5074.

Derivatives and analogs of GW-5074 are also within the scope of the present disclosure.

In embodiments, disclosed compositions can comprise a pharmaceutically acceptable carrier.

Disclosed compositions can further comprise an additional active agent such as, for example, antiviral agents, retrograde transport inhibitors, DNA replication inhibitors, anti-malarials, poly ADP-ribose polymerase 1 inhibitors, tyrosine kinase inhibitors, silencing RNA, cytokines, and combinations thereof.

Various non-exhaustive, non-limiting aspects of compositions according to the present disclosure may be useful alone or in combination with one or more other aspects described herein. Disclosed compositions and methods provide unique advantages to both patients and practitioners.

Methods of Treatment

Disclosed embodiments comprise methods of treating infection, for example viral infections, for example from polyomaviruses. In embodiments, "treating" can comprise reduction in initial JCPyV infection, protection from JCPyV infection, inhibition of JCPyV infection, reduction in symptoms, and combinations thereof.

Disclosed embodiments comprise methods of treating PML. In embodiments, "treating" can comprise reduction in symptoms or disease progression.

Disclosed embodiments comprise methods of treating BKPyV and SV40.

Disclosed methods can comprise selection of a patient particularly suited to benefit, such as, for example, those with multiple sclerosis being treated with immunomodulators, those undergoing renal or bone marrow transplantation, or the like.

In disclosed embodiments, GW-5074 reduces initial infection by JCPyV, for example in primary and immortalized astrocytes.

In disclosed embodiments, the $SI_{50}$ associated with GW-5074 treatment is greater than the threshold that commonly identifies clinical candidates for further development.

In disclosed embodiments, GW-5074 treatment is most effective when administered early in infection.

In disclosed embodiments, GW-5074 potently inhibits viral spread.

The anti-JCPyV activity of GW-5074 may be associated with its antagonistic effects on virus-induced MAPK-ERK signaling.

Disclosed compositions can be administered in a number of appropriate methods. For example, parenteral administration such as via injection can be employed.

In embodiments, oral administration can be employed.

Disclosed compositions can be administered at a therapeutically-appropriate frequency. For example, disclosed methods can comprise administration of a disclosed composition once a day, once a week, once a month, or the like.

Disclosed methods can further comprise identification of a patient at increased risk of developing PML. For example, embodiments comprise identification of a patient with a suppressed immune system, such as a patient taking steroids or suffering from HIV/AIDS.

Disclosed methods can further comprise administration of an additional active agent such as, for example, antiviral agents, retrograde transport inhibitors, DNA replication inhibitors, anti-malarials, poly ADP-ribose polymerase 1 inhibitors, tyrosine kinase inhibitors, silencing RNA, cytokines, and combinations thereof.

Kits

Further embodiments comprise kits, for example kits comprising disclosed compositions for use in disclosed methods. Disclosed kits can further comprise instructions for use, for example use in performing disclosed methods.

Exposure to radiation, such as γ-radiation, may also be carried out in order to sterilize the compositions before or after packaging into the kit.

It should be understood that various changes and modifications to the embodiments described herein will be apparent to those skilled in the art. Such changes and modifications can be made without departing from the spirit and scope of the present subject matter and without diminishing its intended advantages. It is therefore intended that such changes and modifications be covered by the appended claims.

As various changes could be made in the above-described sources and methods without departing from the scope of the invention, it is intended that all matter contained in the above description and in the examples given below, shall be interpreted as illustrative and not in a limiting sense.

EXAMPLES

Example 1

A patient exhibiting early signs of PML is administered a therapeutically effective amount of GW-5074. The patient's difficulty in walking is decreased.

Example 2

A patient exhibiting early signs of PML is administered a therapeutically effective amount of GW-5074. The patient's facial drooping is decreased.

Example 3

A patient exhibiting early signs of PML is administered a therapeutically effective amount of GW-5074. The patient's loss of vision is decreased.

Example 4

A patient exhibiting mid-stage PML is administered a therapeutically effective amount of GW-5074. The patient's seizures are decreased.

Example 5

A patient exhibiting mid-stage PML is administered a therapeutically effective amount of GW-5074. The patient's loss of vision is decreased.

Example 6

A patient who is identified as at risk for the development of PML is administered a therapeutically effective amount of GW-5074. The patient does not develop PML.

Example 7

Pre-treating transformed SVG-A glial cells and primary normal human astrocytes (NHA) with non-toxic concentrations of GW-5074 potently reduced initial JCPyV infection, as evaluated by indirect immune-fluorescent quantification of viral proteins after one round of productive infection.

The 50% inhibitory concentration ($IC_{50}$) associated with GW-5074 treatment was 6.8 μM and 0.84 μM in SVG-A and NHA cells, respectively. GW-5074 was well-tolerated by both cell lines, as the 50% cytotoxic concentration ($CC_{50}$) associated with GW-5074 treatment was greater than 100 μM and 20 μM in SVG-A and NHA cells, respectively.

Using these values, we calculated the minimum 50% selectivity index ($SI_{50}$), defined as the ratio between the $CC_{50}$ and $IC_{50}$, associated with GW-5074 to be 11.8 in SVG-A cells and 20.2 in NHAs. $SI_{50}$ values are important metrics in drug discovery, and an $SI_{50}$ greater than 10 is commonly considered to be an important starting point in drug development. The $SI_{50}$ associated with GW-5074 treatment is larger than the $SI_{50}$ values associated with established compounds with anti-JCPyV activity, including chlorpromazine ($SI_{50}$=2.0), mefloquine ($SI_{50}$=4.0), and Retro-$2^{cycl}$ ($SI_{50}$=7.4). Importantly, GW-5074 also inhibited long-term cell-to-cell spread of JCPyV when introduced after establishment of a productive infection. This result suggests that GW-5074 could be used to control PML in vivo, as most patients support uncontrolled virus replication before symptom onset.

Because GW-5074 is known to inhibit c-Raf, we suspected that the antiviral activity of GW-5074 was associated with its antagonistic effects on MAPK-ERK signaling. We observed that GW-5074 inhibited endogenous ERK phosphorylation, and that ERK activity could not be restored upon coincubation with the Protein Kinase C (PKC) agonist phorbol 12-myristate 13-acetate (PMA). PKC directly activates c-Raf, so these results are consistent with the known signaling antagonism of GW-5074. Similar results were obtained in the context of virus infection, as JCPyV infection could not be rescued by cotreating SVG-A cells with PMA and GW-5074. Taken together, these data support the hypothesis that GW-5074 disrupts MAPK-ERK signaling events needed to establish a productive JCPyV infection.

Disclosed Embodiments

Embodiment 1) A method of treating polyomavirus infection comprising administration of a therapeutically effective amount of GW-5074.

Embodiment 2) The method of embodiment 1, wherein said polyomavirus comprises JCPyV.

Embodiment 3) The method of embodiment 2, wherein said treating reduces JCPyV infection.

Embodiment 4) The method of embodiment 2, wherein said treating reduces JCPyV progression.

Embodiment 5) The method of embodiment 2, wherein said treating inhibits JCPyV progression.

Embodiment 6) A method of treating JC polyomavirus (JCPyV)-associated progressive multifocal leukoencephalopathy (PML) comprising administration of a therapeutically effective amount of GW-5074.

Embodiment 7) The method of embodiment 6, wherein said treating reduces JCPyV infection.

Embodiment 8) The method of embodiment 6, wherein said treating results in protection from JCPyV infection.

Embodiment 9) The method of embodiment 6, wherein said treating inhibits JCPyV infection.

Embodiment 10) The method of embodiment 6, wherein said treating reduces a PML symptom.

Embodiment 11) The method of embodiment 10, wherein said symptom comprises clumsiness or loss of coordination, difficulty walking, facial drooping, loss of vision, personality changes, trouble speaking, weak muscles, or seizures.

Embodiment 12) A method of inhibiting endogenous ERK1/2 phosphorylation comprising administering a therapeutically effective amount of GW-5074 to a patient.

Embodiment 13) The method of embodiment 10, wherein said patient is an immunosuppressed patient.

Embodiment 14) A kit comprising GW-5074 and instructions for use in treating PML.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, comprising the best mode known to the inventor for carrying out the methods and devices described herein. Of course, variations on these described embodiments will become apparent to those of ordinary skill in the art upon reading the foregoing description. Accordingly, this disclosure comprises all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be comprised in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

We claim:

1. A method of treating polyomavirus infection comprising administration of a therapeutically effective amount of GW-5074.

2. The method of claim 1, wherein said polyomavirus comprises JCPyV.

3. The method of claim 2, wherein said treating reduces JCPyV infection.

4. The method of claim 2, wherein said treating reduces JCPyV progression.

5. The method of claim 2, wherein said treating inhibits JCPyV progression.

6. A method of treating JC polyomavirus (JCPyV)-associated progressive multifocal leukoencephalopathy (PML) comprising administration of a therapeutically effective amount of GW-5074.

7. The method of claim 6, wherein said treating reduces JCPyV infection.

8. The method of claim 6, wherein said treating results in protection from JCPyV infection.

9. The method of claim 6, wherein said treating inhibits JCPyV infection.

10. The method of claim 6, wherein said treating reduces a PML symptom.

11. The method of claim 10, wherein said symptom comprises clumsiness or loss of coordination, difficulty walking, facial drooping, loss of vision, personality changes, trouble speaking, weak muscles, or seizures.

12. The method of claim 10, wherein said patient is an immunosuppressed patient.

* * * * *